United States Patent [19]

Ichinomiya et al.

[11] 4,372,319
[45] Feb. 8, 1983

[54] LOW FREQUENCY THERAPEUTIC INSTRUMENT

[75] Inventors: Tsutomu Ichinomiya; Mamoru Hosoe; Masayoshi Nagayama; Hirotaka Chousa; Rokusaburo Kimura, all of Kadoma, Japan

[73] Assignee: Matsushita Electric Works, Ltd., Osaka, Japan

[21] Appl. No.: 237,126

[22] PCT Filed: Jun. 13, 1980

[86] PCT No.: PCT/JP80/00130
§ 371 Date: Feb. 17, 1981
§ 102(e) Date: Feb. 17, 1981

[87] PCT Pub. No.: WO80/02803
PCT Pub. Date: Dec. 24, 1980

[30] Foreign Application Priority Data
Jun. 15, 1979 [JP] Japan .................................. 54-75934

[51] Int. Cl.³ .............................................. A61N 1/36
[52] U.S. Cl. .................................... 128/421; 128/422

[58] Field of Search ................................ 128/421–423, 128/303.18, 419 R

[56] References Cited

U.S. PATENT DOCUMENTS

| 3,050,695 | 8/1962 | Du Vell | 128/421 X |
| 3,054,405 | 9/1962 | Tapper | 128/303.18 |
| 3,241,557 | 3/1966 | Masaki | 128/422 |
| 3,645,267 | 2/1972 | Hagfors | 128/421 |
| 4,102,348 | 7/1978 | Hihara et al. | 128/422 |
| 4,224,944 | 9/1980 | Roberts | 128/303.18 |
| 4,301,794 | 11/1981 | Tapper | 128/419 R X |

Primary Examiner—Lee S. Cohen
Attorney, Agent, or Firm—Burns, Doane, Swecker & Mathis

[57] ABSTRACT

A low frequency therapeutic instrument of the present invention which performs therapies by applying low frequency pulses to a human body can automatically elevate the voltage of low frequency output gradually from a low voltage by detecting contact connections with a patient of an output terminal for applying a low frequency to the patient so as to reduce any shock to the patient at the time of starting the therapy.

4 Claims, 10 Drawing Figures

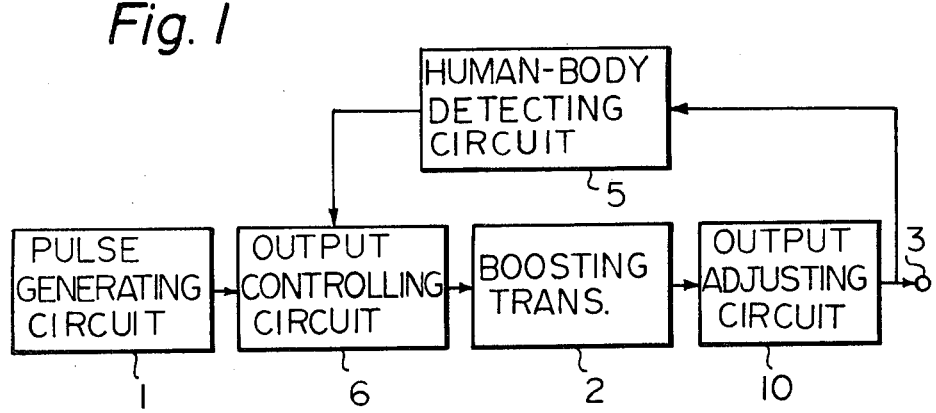
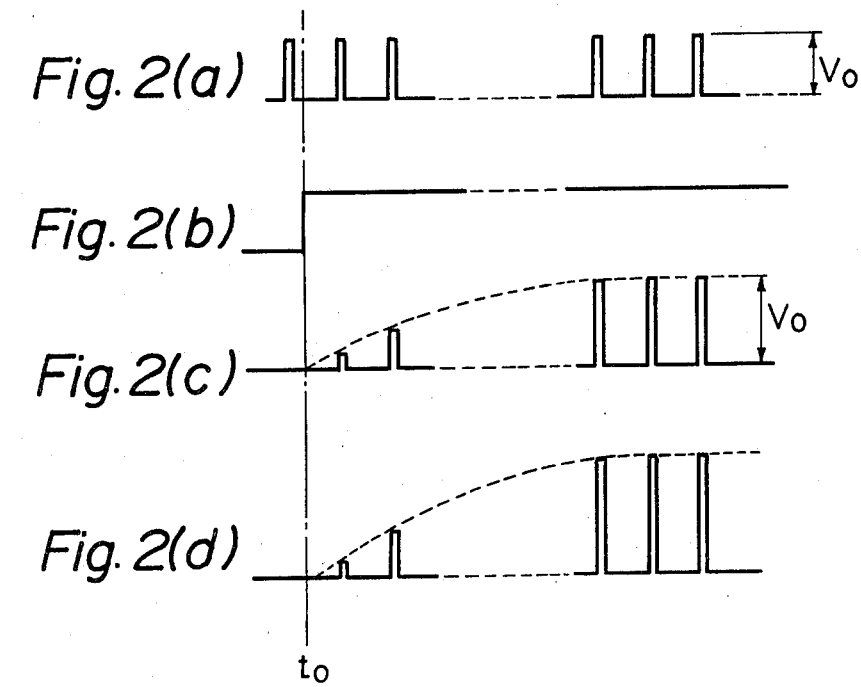

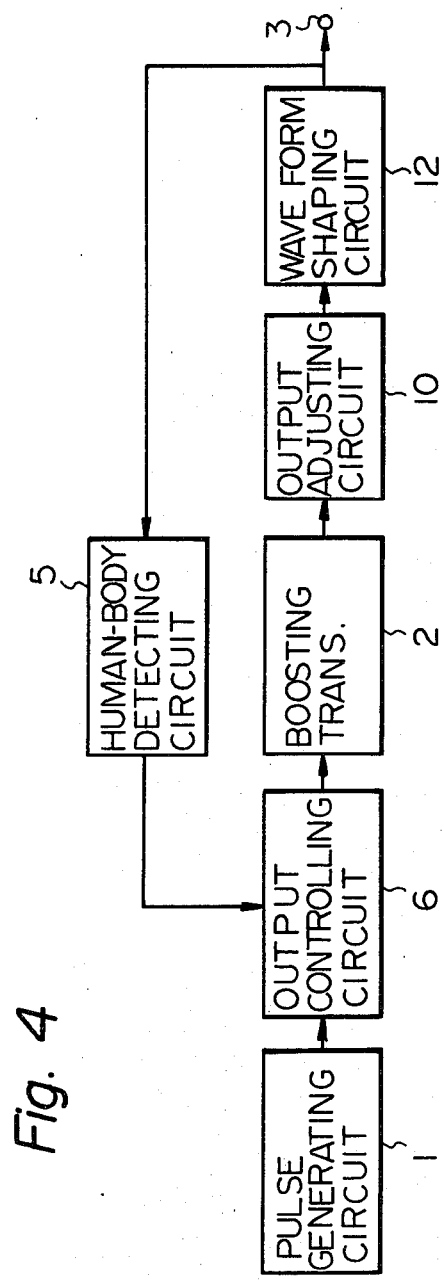
Fig. 4
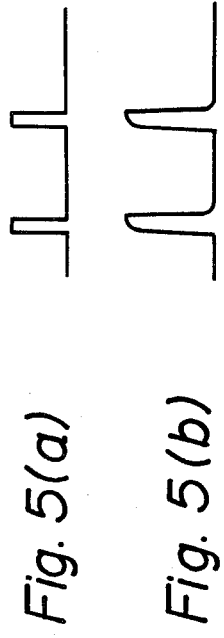
Fig. 5(a)
Fig. 5(b)

LOW FREQUENCY THERAPEUTIC INSTRUMENT

FIELD OF ART

This invention relates to low frequency therapeutic instruments for performing therapies by applying to human body an electricity in the form of low frequency pulses.

BACKGROUND ART

In applying a low frequency to a patient in the case of conventional low frequency therapeutic instruments, if the low frequency of a high voltage is given from the beginning, it will not only shock and discomfort the human body but will be also sometimes even detrimental, and general usage of these therapeutic instruments has been such that the user gradually elevates the output of low frequency pulses with the volume or the like of an output adjusting circuit to use the instrument at a proper voltage. This is also the same in the case that the therapy of one portion of the human body ends and then a conductor is contacted with another body portion, thus the voltage must be elevated to a proper level at each time through a manual adjustment, and there has been involved a problem that the handling is complicate.

Further, in the conventional low frequency therapeutic instruments, the output wave form of the low frequency pulses is generally a rectangular wave form which is not particularly shaped in the wave form, and there has been a problem that a pain will be given to the patient in the rising part of the wave form.

DISCLOSURE OF THE INVENTION

A primary object of the present invention is, therefore, to provide a form very simple to handle a low frequency therapeutic instrument which shocks little the human body at the time of starting the therapy and is comfortable.

A secondary object of the present invention is to provide a low frequency therapeutic instrument with which, even if the portion of the human body to which the low frequency is applied is often changed, the foregoing function can be ensured.

A third object of the present invention is to provide a low frequency therapeutic instrument which realizes a therapy with less pain during the therapy.

Now, in the present invention, the primary object is attained by detecting a contact of the patient with a conductor and controlling the low frequency pulse voltage with such detection signal so as to gradually elevate the voltage to be applied to the patient from a low voltage to a predetermined voltage, the second object is attained by detecting a separation of the patient from the conductor and reducing the low frequency pulse voltage to a low voltage and, further, the third object is attained by shaping the low frequency pulse output wave form so as to be rounded.

Preferred embodiments of the present invention will be described in the following detailed description with reference to the drawing.

BRIEF DESCRIPTION OF THE DRAWING

FIG. 1 is a block diagram of a first embodiment of the present invention;

FIG. 2(a) is a time chart of the pulse generating circuit output of the first embodiment;

FIG. 2(b) is a time chart of the human-body detecting circuit output of the first embodiment;

FIG. 2(c) is a time chart of the output controlling circuit output of the first embodiment;

FIG. 2(d) is a time chart of the low frequency output of the first embodiment;

FIG. 4 is a block diagram of a second embodiment of the present invention;

FIG. 5(a) is a time chart of the output adjusting circuit output of the second embodiment;

FIG. 5(b) is a time chart of the pulse output terminal output of the second embodiment.

DETAILED DESCRIPTION OF THE PREFERRED EMBODIMENTS

Figure 3:
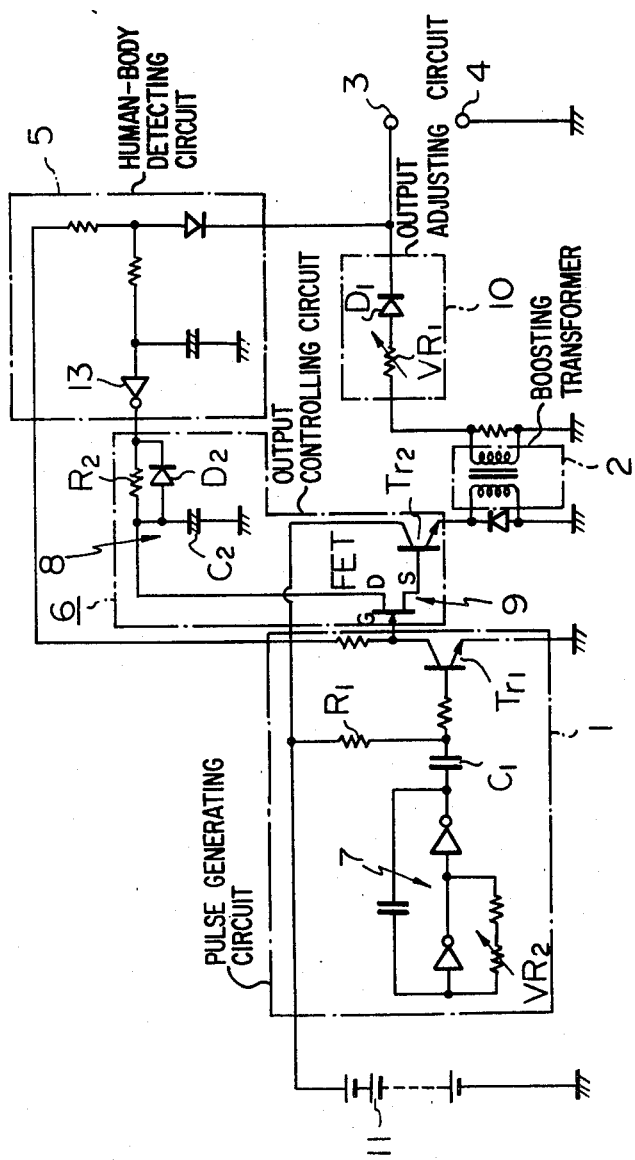
FIG. 3 is a circuit diagram of the first embodiment.

FIG. 1 shows a block diagram of an embodiment of the present invention, which is formed in such that a pulse generating circuit 1, a boosting transformer 2 and an output adjusting circuit 10 formed of a variable resistor and the like are made to be a basic formation, to which a human-body detecting circuit 5 and an output controlling circuit 6 are added, and the output of the output adjusting circuit 10 is connected to a pulse output terminal 3 to which a low frequency therapeutic conductor (not illustrated) is electrically connected to be used for the low frequency therapy. The pulse generating circuit 1 is formed of an oscillating circuit 7 as a center as shown, for example, in FIG. 3 of a practical circuit diagram and provides as outputs low frequency pulses of a voltage $V_o$ equal to the voltage of a battery 11 which is variable in the pulse width in the range of 0.2 to 0.3 m.sec. and in the repeating cycle in the range of 30 m.sec. to 1 sec. as shown in a time chart (a) of FIG. 2. In the practical circuit of FIG. 3, the oscillating cycle of the oscillating circuit 7 is made variable in the range of 30 m.sec. to 1 sec. by adjusting a variable resistor $VR_2$, the square wave output of this oscillating circuit 7 is differentiated with a differentiating circuit comprising a capacitor $C_1$ and resistor $R_1$ to provide differential pulses of a pulse width of about 0.2 to 0.3 m.sec. and these pulses are amplified with transistors $TR_1$ and $TR_2$ and are applied to the primary side of the boosting transformer 2 to obtain a low frequency pulse output of about 120 V as its secondary output. Here, while the gate G and source S of a field-effect transistor FET forming an amplification controlling circuit 9 of the output controlling circuit 6 are inserted between the transistors $TR_1$ and $TR_2$, details of this output controlling circuit 6 shall be described later. Thus the secondary output of the boosting transformer 2 is connected at one end to the pulse output terminal 3 through a variable resistor $VR_1$ forming the output adjusting circuit 10 and at the other end to an earthing terminal 4 so that the peak value of the low frequency pulses provided at the pulse output terminal 3 can be varied in the range of 30 to 120 V by properly adjusting the variable resistor $VR_1$. In the output adjusting circuit 10, further, a diode $D_1$ connecting in series with the variable resistor $VR_1$ is to prevent any reverse current flow upon the detection of the contact of the human body with the conductor by applying a voltage of battery 11 to the pulse output terminal 3 and earthing terminal 4 by means of the human-body detecting circuit 5. As described above, the human-body detecting circuit 5 is made to detect whether the human body has contacted the conductor, that is, the pulse output terminal 3 by applying the voltage of the battery 11 between the pulse output terminal 3 and the earthing terminal 4 and measuring the resistance value between the both terminals 3 and 4 and, provided that, in the time charts of FIG. 2, the conductor is caused to contact the human body at a time $t_o$, such output wave form as shown in FIG. 2(b) is obtained in the human-body detecting circuit 5. In the output controlling circuit 6, such input signal as shown in FIG. 2(b) is integrated with an integrating circuit part 8 comprising a resistor $R_2$ and capacitor $C_2$ to obtain a voltage signal which gradually rises requiring about 2 to 3 sec. from the time $t_o$ and this voltage signal is applied to the drain D of the field effect transistor FET so that, in the amplification controlling circuit 9, the voltage value of the low frequency pulses transmitted from the transistor $TR_1$ to the transistor $TR_2$ will be gradually elevated as in FIG. 2(c) and thereby the voltage of the low frequency pulses of the pulse output terminal 3 applied to the conductor will be gradually elevated as in FIG. 2(d), whereby any shock at the time of starting the therapy will be reduced.

When the conductor separates from the human body, further, it is detected by the human-body detecting circuit 5, the output of this human-body detecting circuit 5 is made zero and the voltage of the low frequency pulses of the pulse output terminal 3 is reduced to 0 V, whereby the output is made free of any necessity of being adjusted upon each change of the therapy position and the therapeutic operation is made simpler. Further, at this time, the electric charge of the capacitor $C_2$ of the integrating circuit part 8 charged during the therapy is quickly discharged to an earthing part of an inverter 13 forming the human-body detecting circuit 5 through a diode $D_2$ so that the voltage of the low frequency pulses will quickly fall.

Figure 6:
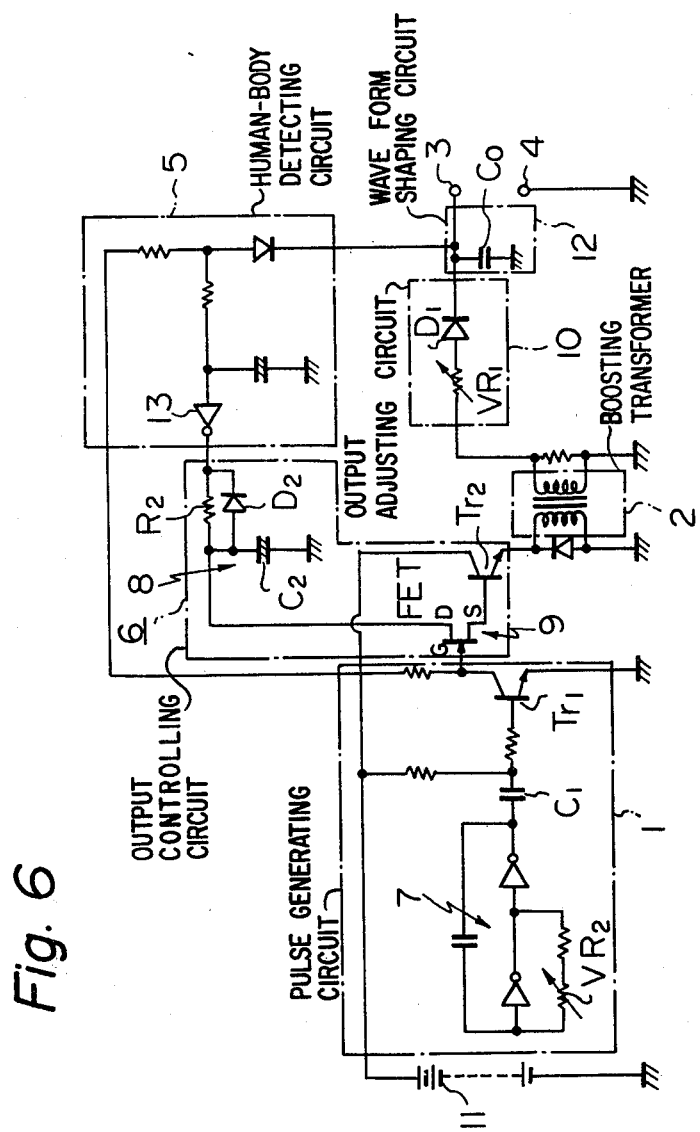
FIG. 6 is a circuit diagram of the second embodiment.

FIG. 4 is a block diagram showing another embodiment of the present invention, wherein a wave form shaping circuit 12 is provided between the pulse output terminal 3 and the output adjusting circuit 10, this wave form shaping circuit 12 is formed by connecting a capacitor $C_o$ between the low frequency output terminal 3 and the output adjusting circuit 10 as shown in FIG. 6, and such rectangular low frequency pulse wave form as shown in FIG. 5(a) is integrated with an integrating circuit formed by the capacitor $C_o$ and the resistance of the human body so that, as shown in FIG. 5(b), the rise of the pulse wave form at the pulse output terminal 3 will be delayed and a rounded output will be obtained, whereby the pain incurred during the therapy is made smaller and a pleasant therapy can be performed. The position of inserting the wave form shaping circuit 12 is not limited to that in the foregoing embodiment but may well be between the pulse generating circuit 1 and the pulse output terminal 3.

We claim:

1. Low frequency therapeutic apparatus for applying low frequency pulses to a human body comprising pulse generating means for producing a low frequency pulse output, control means for controlling said pulse output in response to a control signal such that a controlled pulse output is produced, terminal means connected to said control means for applying said controlled pulse output to a human body, human body detecting means responsive to contact of said terminal means with a human body for automatically producing said control signal such that the amplitude of said controlled pulse output is gradually increased from a low value to a predetermined operating value.

2. The therapeutic apparatus of claim 1 wherein said control means comprises amplifier means for amplifying said pulse output and means responsive to said control signal for controlling the amplification of said amplifier means.

3. The therapeutic apparatus of claim 2 wherein said human body detecting means comprises charging means for gradually varying said control signal to increase the amplitude of said controlled pulse output, which charging means is charged when said terminal means contacts a human body, and discharging means for automatically discharging said charging means upon separation of said terminal means from a human body.

4. The therapeutic apparatus of claim 1 further comprising wave form shaping means connected so as to shape the pulses applied by said terminal means.

* * * * *